(12) United States Patent
Heilek et al.

(10) Patent No.: US 7,323,016 B2
(45) Date of Patent: Jan. 29, 2008

(54) REGULATION OF A WASH COLUMN IN A MELT CRYSTALLIZATION PROCESS

(75) Inventors: Jörg Heilek, Bammental (DE); Bernd Eck, Viernheim (DE); Dieter Baumann, Walldorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 722 days.

(21) Appl. No.: 10/333,721

(22) PCT Filed: Jul. 27, 2001

(86) PCT No.: PCT/EP01/08712

§ 371 (c)(1),
(2), (4) Date: Jan. 24, 2003

(87) PCT Pub. No.: WO02/09839

PCT Pub. Date: Feb. 7, 2002

(65) Prior Publication Data

US 2003/0175159 A1    Sep. 18, 2003

(30) Foreign Application Priority Data

Jul. 28, 2000    (DE) .............................. 100 36 880

(51) Int. Cl.
*C30B 7/08* (2006.01)
(52) U.S. Cl. ...................... 23/295 R; 23/305 A; 134/5; 134/13; 134/18; 422/245.1; 422/105; 117/68; 117/69

(58) Field of Classification Search ................. 134/5, 134/13, 18; 23/295 R, 305 A; 422/105, 422/245.1; 117/53, 68, 69
See application file for complete search history.

(56) References Cited

U.S. PATENT DOCUMENTS 4,914,310 A * 4/1990 Jarofski ...................... 250/574
5,569,808 A    10/1996 Hotier et al.

FOREIGN PATENT DOCUMENTS

| DE | 197 41 307 | 4/1999 |
|---|---|---|
| EP | 0 491 558 | 6/1992 |
| GB | 2 023 564 | 1/1980 |
| JP | 60 195437 | 10/1985 |
| WO | 98 27240 | 6/1998 |

OTHER PUBLICATIONS

Derwent Abstract DE 19741307A, Apr. 1999.*
U.S. Appl. No. 10/333,721, filed Jan. 24, 2003, Heilek et al.
U.S. Appl. No. 10/494,721, filed May. 6, 2004, Hammon, et al.

* cited by examiner

*Primary Examiner*—Robert Kunemund
(74) *Attorney, Agent, or Firm*—Oblon, Spivak, McClelland, Maier & Neustadt, P.C.

(57) ABSTRACT

The present invention relates to the use of an optical line detector for regulating the position of the wash front and/or of the build-up front of the crystal bed of a wash column in a melt crystallization process and a corresponding regulation method. The line detector, for example a CCD camera or a linear array of reflection probes, is arranged in such a way that optical properties of the crystal bed can be detected continuously in a region running parallel to the longitudinal axis of the wash column, this region covering the desired setpoint position of the wash front or of the build-up front.

18 Claims, 2 Drawing Sheets

REGULATION OF A WASH COLUMN IN A MELT CRYSTALLIZATION PROCESS

The present invention relates to the regulation of a wash column in a melt crystallization process, in particular the use of an optical line detector for such regulation, and a corresponding regulating method and an apparatus for carrying out the regulating method.

The purity of products produced in the chemical industry is having to meet increasingly high requirements. This applies not only to the fine chemicals or to pharmaceuticals but increasingly also to mass products, in particular to substances which are used as starting materials in the polymer industry, for example acrylic acid, caprolactam, naphthalene or phenol. Purity requirements of more than 99.99% by weight are not unusual for such substances since only highly pure starting materials permit precise control of the chain length distribution of the polymers, which in turn is decisive for the specific properties of the polymers.

In the synthesis of a chemical compound, the desired substance is however not usually obtained as pure product but is part of a mixture of compounds which contains impurities, such as solvents, starting compounds, byproducts and undesired isomers, in addition to the desired substance. For the separation of the desired substance from the impurities, distillative separation methods are frequently used on the industrial scale but are associated with high energy consumption.

If the desired substance is a crystallizable compound which is present in a liquid mixture of compounds after the synthesis process, melt crystallization is a possible method for purifying the desired substance, i.e. for separating the substance from the liquid mixture of compounds. The desired compound is crystallized as a solid from the liquid and the crystalline solid is then separated from the remaining liquid, which is referred to as the mother liquor, and is melted again. The melt is then removed as purified desired product. Conventional methods of the prior art are static and dynamic layer crystallization, in which the compound to be isolated is deposited on stationary, cooled surfaces, or suspension crystallization, which is based on the growth of crystals in a suspension. Compared with layer crystallization, suspension crystallization has the advantage that it can be carried out in a continuous process. Moreover, the purity of the crystals is very high owing to their comparatively slow rate of growth. In spite of the slower rate of growth, a high product throughput can be achieved by means of suspension crystallization, since crystallization in solution is associated with a large total surface area available for growth.

Suspension crystallization is therefore a very effective and economical method for achieving high purity of the desired compound. Use is made of the fact that impurities are substantially displaced from the crystal lattice during the growth of the crystals in a liquid and remain behind in the mother liquor. Even in a one-stage crystallization process, highly pure crystals of the desired compound are therefore obtained.

The decisive step which critically influences the purity of the end product is the separation of the highly pure crystals from their mother liquor, which contains the impurities and the uncrystallized fractions of the original mixture, by a solid/liquid separation process. This separation process can take place in a plurality of stages, a wash column usually being used at least in the final stage. The object of the wash column is to separate the resulting pure crystal phase as completely as possible from the mother liquor. For this purpose, the crystal suspension produced in a crystallizer is passed into the wash column and a denser crystal bed is produced by removing mother liquor. A wash liquid, for example a melt of the molten crystals themselves, is passed countercurrently through the crystal bed.

Various methods are used for forming a compact crystal bed. In the case of wash columns operating under gravity, the crystal suspension is introduced into the column from the top and the crystal bed forms in a sedimentation process. In such columns, however, there is the danger that vertical channels form in the course of the sedimentation process, in which channels back-mixing of the mother liquor or of the crystal suspension with the wash liquid occurs. Wash columns operating under gravity are therefore generally provided, over a part of their height, with a stirrer which prevents the formation of vertical liquid channels in the crystal bed.

Such stirrers are not required in hydraulic or mechanical wash columns. In hydraulic wash columns, the suspension is instead transported under pressure into a pressure-tight wash column. The transport pressure itself then ensures compaction of the crystals to give a dense fixed bed. In a mechanical wash column, the pressure for the formation of a dense crystal bed is generated, for example, by a mechanical, semipermeable ram which is permeable to mother liquor but impermeable to the crystals in the suspension fed in. The compaction to give a crystal bed can however also be effected by separating off the mother liquor via filters and mechanically transporting the crystals from the filter to the crystal bed by a rotating transport element.

The crystal bed has a build-up front on which crystals of the crystal suspension fed in continuously accumulate. The build-up front thus describes the transition from the suspension to the crystal bed and is characterized by a relatively abrupt increase in the crystal content in the suspension. In hydraulic wash columns, this build-up front is also referred to as a filtration front.

At that end of the crystal bed which is opposite to the build-up front, a type of rotor blade or scraper, which continuously removes crystals from the dense crystal bed, is generally arranged. Through the continuous accumulation of crystals at the build-up front on the one hand and the continuous removal of crystals at that end of the crystal bed which is opposite to the build-up front, on the other hand a transport direction of the crystal bed is defined. The crystals removed from the crystal bed are melted in a heat exchanger. A part of the melt is removed as pure product stream and another part of the melt is passed as a wash liquid stream through the crystal bed in a direction opposite to the transport direction of the crystals.

By transporting the melt in a direction opposite to that of the crystal bed, countercurrent washing of the crystals is effected. The purification of the crystals is based essentially on displacement and dilution of the mother liquor in the voids of the crystal bed by the wash liquid. The dilution effect is based here on mixing in the voids between the crystals through which flow takes place and on diffusion in the contact areas where there is no through-flow or in the surface-near flow boundary layer of the crystals. In steady-state operation, a wash front, which is defined as that point in the wash column where the highest temperature and concentration gradients occur, is established at a defined height of the crystal bed. At the height of the wash front, in fact, a concentration transition from mother liquor concentration (above the wash front) to pure melt concentration (below the wash front) takes place in the liquid surrounding the crystals. In order to achieve an adequate purification effect, the wash front must be positioned at a specific minimum height above the scraper. Since the crystallization temperature in the contaminated suspension is below the melting point of the pure product, the temperature equilibration of the cold crystals with the pure wash liquid additionally occurs in the region of the wash front, during which the wash liquid partially or completely recrystallizes. Consequently, at least a part of the wash liquid can be recovered. This recrystallization of the wash liquid is particularly effective if the crystallization temperature in the mother liquor is from about 10 to 15 K. below the melting point of the pure product.

In order to ensure stable operation of a wash column, i.e. to ensure a defined space-time yield with a constantly good purification effect, continuous compensation of external disturbance variables is required. Such disturbance variables may be, for example, variations in the amount of suspension, changes in the crystal content in the suspension, variation of the crystal size distribution or concentration variations in the product mixture fed to the crystallizer from the synthesis process.

The compensation of such external disturbances is usually effected:
- by regulation of the heat of fusion;
- by adapting the specific amount of wash liquid by means of regulation of the position of the wash front;
- and, in the case of hydraulic and gravity wash columns, additionally by regulation of the position of the build-up front.

In order to control the purity of the pure product melts, for example, an extinction sensor which determines the extinction in a spectral range characteristic of the desired product can additionally be arranged in a product take-off line or in a line of the melt circulation. If the extinction sensor is arranged in a line of the melt circulation, it can also be used for starting up the wash column, so that, on starting up, it is possible to determine the time when the product valve is opened for the first time.

The regulation of the heat of fusion, i.e. the introduction of the required quantity of heat for melting the crystals in the melt circulation is usually ensured by regulating the product temperature after the heat exchanger. The temperature in the melt circulation immediately after the heat exchanger is preferably about 1-5 K. above the melting point of the pure product. The rotor blade or the scraper is usually operated at a fixed speed. Suitable methods for regulating the heat of fusion are known to the person skilled in the art and do not form the subject matter of the present invention.

The present invention relates instead to the regulation of the position of the wash front and/or the position of the build-up front of the crystal bed.

A constant position of the wash front in the crystal bed ensures that a sufficiently large amount of wash liquid flows countercurrent to the transport direction of the crystal bed so that a specific purity of the end product can be achieved. A specific amount of wash liquid is defined as that amount of wash liquid which is to be used within a specific time interval for achieving a defined separation effect, based on the amount of crystals fed to the wash column in this time interval. Conventionally, the specific amount of wash liquid is set by regulating the position of the wash front below the filter in the column. The wash front is regulated to a defined position between the filter and the scraper by adjusting the amount of wash liquid via the product valve. This ensures that a desired separation effect, i.e. a specific product purity, is achieved with minimum use of wash liquid. For detection of the wash front, for example, one or more temperature sensors arranged in the crystal bed can be used since the temperature transition from the crystallization temperature to the melt temperature of the pure product takes place at the height of the wash front. Alternatively, optical sensors, for example reflection probes, can also be used for detecting the position of the wash front. The liquid surrounding the crystal bed substantially comprises contaminated mother liquor above the wash front and, on the other hand, pure product melt below the wash front. Depending on the type of substances involved, measurable changes in the optical properties, for example the reflection properties, can occur during this transition. As in the case of the regulation of the build-up front, the wash front is usually regulated between two reflection sensors an axial distance apart.

A constant position of the build-up front ensures that the external mass balance of the wash column is always maintained, i.e. it is ensured in this case that the same amount of molten pure product is removed or is lost from the wash column with the mother liquor as the amount of crystals newly entering the wash column. The position of the build-up front in the wash column is usually determined with the aid of two optical reflection sensors which are arranged a certain axial distance apart (i.e. measured along the longitudinal axis of the wash column) at a defined height in the cylindrical side wall of the wash column. The position of the build-up or filtration front can be influenced, for example in the case of hydraulic wash columns, by adjusting the hydraulic conditions in the wash column. If, for example, mother liquor is removed continuously from the wash column via corresponding filters, it is possible to pump part of this removed mother liquor back into the column for influencing the hydrodynamic pressure in said column. The recycled amount of mother liquor, which can be varied by means of a corresponding pilot pump, for example by a speed change, is adjusted. If, for example, the upper reflection sensor indicates that the crystal bed is rising in the wash column, a control circuit increases the quantity of control current. Correspondingly, the quantity of control current is reduced when the bed is falling. The change in the quantity of control current is carried out according to a defined characteristic, for example linearly as a function of flow rate and time.

The two reflection sensors, which are usually used for regulating the wash front or build-up front, typically have an axial spacing (i.e. measured along the longitudinal axis of the wash column), of from 5 to 10 cm, in the case of wash columns having a crystal bed about 1 m high. This distance must on the one hand be chosen to be sufficiently large so that the difference between the signals delivered by the two sensors is large enough for regulation. On the other hand, the distance between the two reflection sensors also corresponds to the accuracy with which the position of the build-up front can be regulated. The known regulation concept with the aid of two axially separated optical sensors has the disadvantage that the position of the fronts can be regulated only very inaccurately within a relatively wide range defined by two boundary values. This disadvantage is particularly marked when the optical changes occurring at the build-up front or the wash front are small. This is the case, for example, when starting up a wash column, if the fronts initially form in the course of time but, for example, also during ongoing operation if an already relatively pure starting material is to be further purified by melt crystallization. Moreover, the known 2-point regulation is relatively unstable so that relatively large disturbances can readily lead to failure of the regulation.

It is an object of the present invention to provide a method and an apparatus for regulating a wash column in a melt crystallization process, it being possible to regulate the position of the wash front and/or of the build-up or the filtration front with relatively high accuracy. Moreover, reliable regulation may be permitted even when only small changes in the optical properties of the crystal bed or the liquids running around the crystal bed occur at the wash front or the build-up front.

We have found that this object is achieved by the use of an optical line detector for regulating the position of the wash front and/or of the build-up front in a wash column in a melt crystallization process. According to the invention, the line detector is arranged in such a way that optical properties of the crystal bed in a region running parallel to the longitudinal axis of the wash column can be continuously detected, this region covering the desired setpoint position of the wash front or of the build-up front. The line detector has more than two, preferably more than four and particularly preferably more than 10 measuring elements (sensor cells) so that the axial variation of the optical properties investigated and hence also the position of the build-up or wash front can be determined substantially more precisely than with the known 2-point measurement.

The present invention accordingly also relates to a method for regulating a wash column in a melt crystallization process in which a suspension, which contains, suspended in a mother liquor crystals of a substance to be purified, is passed continuously into a wash column, a crystal bed of crystals of the substance to be purified forms in the wash column, the crystal bed having a build-up front at which crystals of the suspension passed in continuously accumulate, crystals are continuously removed at that end of the crystal bed which is opposite to the build-up front, the crystals removed are melted, a part of the melt is removed as pure product stream and another part of the melt is passed as a wash liquid stream through the crystal bed in the direction opposite to the transport direction of the crystals, a wash front forming in the crystal bed. According to the invention, the method is distinguished by the fact that the position of the build-up front and/or the position of the wash front in the wash column is regulated by means of at least one optical line detector.

Suitable optical line detectors are a wide range of linear sensor arrays with more than two sensor elements which are capable of determining the desired optical properties of the crystal bed. In the case of a typical crystal bed height between build-up front and scraper of 0.5 m in a mechanical wash column, of from 0.5 to 1.5 m in a hydraulic wash column and up to 5 m in a gravity wash column, the control region to be monitored by the line detector is typically from 5 to 30, preferably from 5 to 10, cm. The signals of the individual sensor elements of the line detector are digitized and transmitted to an evaluation means, for example a computer. The evaluation means analyzes the data recorded by the line detector. For example, the position of the build-up or wash front can be determined as the position at which the measured optical signal shows the greatest change (i.e. the point of inflection of the signal curve). The precision of the regulation is thus no longer dependent on a minimum signal difference between adjacent sensors and is therefore substantially higher than in the case of the conventional 2-point regulation.

In addition to the higher accuracy of the regulation of the position of the wash or build-up front, a particular advantage of the invention is that the use of a plurality of sensor elements permits more stable regulation. In fact the more sensor elements which cover the region to be monitored, the more readily can conventional regulation concepts, such as PI regulation (proportional integral regulation) be employed. In contrast to the conventional 2-point regulation, drift components in the measured signal which are caused, for example, by a change in the lamp intensity or by deposits on the sensor surface or on a measurement window in the column wall, can thus also be compensated.

For regulating the position of the wash front, the instantaneous position of the wash front is advantageously measured by means of an optical line detector and regulated to a setpoint position by corresponding control of the pure product stream removed.

If the wash column used in the novel method is a hydraulic wash column, the position of the build-up front can also be determined by means of an optical line detector and can be regulated to a setpoint position by controlling the hydrodynamic pressure in the wash column, for example by recycling mother liquor by means of a pilot pump.

According to a preferred variant of the novel method, at least one linear array of fiber-optic reflection probes is used as the optical line detector. Each of these fiber-optic reflection probes may have, for example, one or more transmitting fibers and one or more receiving fibers. The transmitting fibers are connected at one fiber end to a light source, so that excitation light can be inserted into the fibers. Inserted light can emerge at the other end of the transmitting fibers. The reflection probes are arranged on the cylindrical wall of the wash column in such a way that the light emerging from the transmitting fibers strikes the crystal bed and is partly scattered back to the probe. Each probe also contains receiving fibers which collect the back-scattered light and pass it to a detector system. Instead of separate transmitting and receiving fibers, it is also possible to use a fiber which acts both as a transmitting fiber and as a receiving fiber. However, a Y-shaped branch to the light source and to the detector is then provided at one end of the fibers. The individual linearly arranged reflection probes are not necessarily structurally separate units. Rather, the term reflection sensor means a group of transmitting and receiving fibers which are coordinated with one another and together form a measuring element of the linear array. Thus, each individual reflection probe can form a measuring element of, for example, 1 $mm^2$ in area. With a linear array of 10 such reflection probes arranged 1 cm apart, the front to be regulated can thus be regulated in a stable manner with an accuracy of 1 cm.

According to another variant of the novel method at least one line camera, in particular a CCD line camera, is used as the optical line detector. In this case, one or more elongated inspection windows which can be focussed onto the CCD line chip via the imaging optical system of the camera are arranged in the cylindrical wall of the wash column. In this case, an illumination means which illuminates the inspection window and the crystal bed behind it is usually also used.

Depending on the optical properties of the materials to be separated in the wash column, it is possible with the aid of suitable filters, which may be arranged both in the illumination means and in the detector of the reflection probe or in the imaging optical system of the line camera, to select spectral ranges in which particularly large signal changes can be expected. It is also possible to use, for example, a CCD color camera in which each measuring element is represented by three CCD chips having different spectral sensitivity. In the purification of acrylic acid by melt crystallization, for example, the position of the wash front is preferably determined by measuring the reflection in a spectral range of from 300 to 400 nm.

The present invention also relates to an apparatus for separating crystals and mother liquor in a suspension crystallization process, which apparatus is particularly suitable for carrying out the novel method. The apparatus comprises a wash column, which has at least one feed line for a crystal suspension, filtration means for removing mother liquor and means for removing crystals from a crystal bed, means for melting the crystals removed, a take-off means for removing a part of the melt as a pure product stream, at least one measuring means for determining the position of a build-up front and/or a wash front of the crystal bed in the wash column and means for regulating the position of the build-up front and/or the position of the wash front, wherein, in the novel apparatus, the measuring means comprises at least one optical line detector.

According to one embodiment of the novel apparatus, the optical line detector comprises a linear array of more than two, preferably more than four, and particularly preferably more than 10 fiber-optic reflection probes which are arranged in a wall of the wash column.

According to another embodiment, at least one transparent window is arranged in the wall of the wash column, and the optical line detector comprises at least one line camera which is oriented toward the transparent window. Particularly preferably, the line camera is a CCD line camera, for example a color CCD line camera. Such line cameras are commercially available and typically have 1024 or 2048 linearly arranged pixels. The area of a pixel is typically of the order of from 50 to 100 µm².

The novel method and the novel apparatus are suitable for all types of wash columns in which a wash front and/or a build-up or filtration front forms during operation, in particular for hydraulic, mechanical or gravity wash columns. Preferably, the present invention is used in melt crystallization processes in which a melt of the pure product is used as wash liquid, but the novel regulation principle can also be used when liquids other than a product melt are used as wash liquids.

The present invention is illustrated in more detail below with reference to embodiments shown in the attached drawings.

Figure 1:
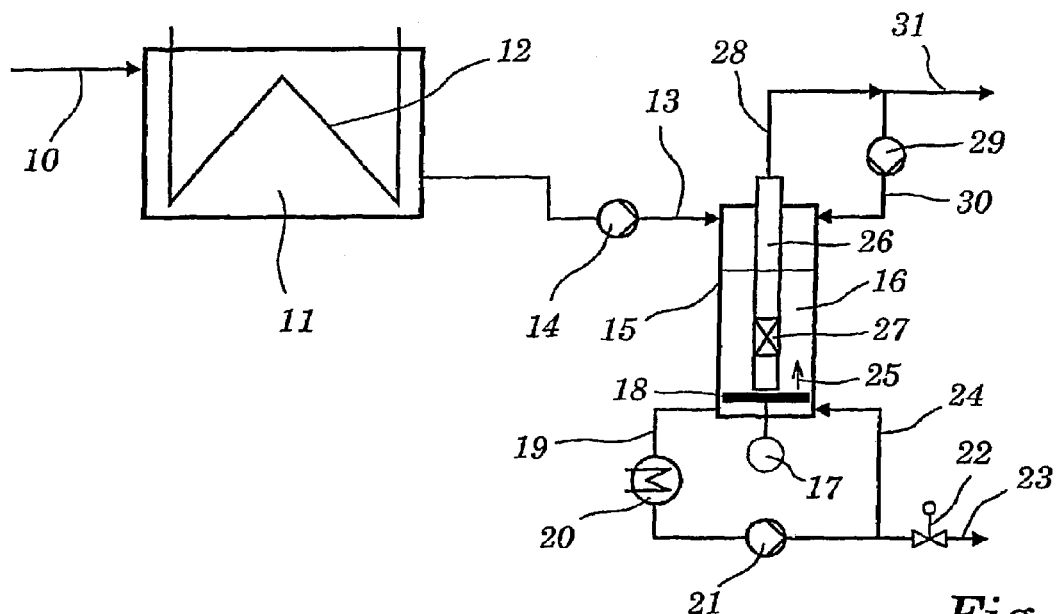
FIG. 1 shows a schematic overview of a suspension crystallization process.

FIG. 1 shows the schematic design of a plant, known per se, for purifying synthesis products by suspension crystallization. A liquid product mixture originating from a synthesis process (not shown) is fed to a crystallizer 11 via a line 10. The crystallizer 11 contains a heat exchanger 12 which withdraws heat from the product mixture. In the liquid, crystals of the desired compound begin to grow. The crystal suspension (crystals and mother liquor) formed in the crystallizer 11 is transported, by means of a pump 14 arranged in a connecting line 13, into a wash column 15, which is in the form of a hydraulic wash column in the example shown. The mode of operation of the wash column 15 is explained in more detail below in association with the detailed diagram of FIG. 2. Essentially, the crystals of the suspension fed in are compacted in the wash column 15 to give a dense crystal bed which, in the case of the hydraulic wash column shown, is in the form of a fixed bed 16. Arranged at the lower end of the fixed bed 16 is a scraper 18 which is driven by a motor 17 and continuously removes crystals from the fixed bed. The crystals enter a melt circulation 19 in which a heat exchanger 20 and a pump 21 are arranged and are melted there. Via an adjustable product valve 22, a part of the melt is removed from the melt circulation 19 as desired pure product through a line 23. The other part of the melt is recycled via a line section 24 of the melt circulation 19 into the wash column 15 and can flow through the fixed bed 16 partly as wash liquid, countercurrently to the direction of transport of the crystals. The direction of flow of the wash liquid is indicated by an arrow 25 in FIG. 1.

One or more vertical drainpipes 26 which are each provided with a filter 27 at a definite height, arranged in the wash column 15. Substantially the mother liquor but, if required, also a part of the melt flowing as wash liquid from the lower region of the column to the filters (arrow 25) or very small crystallite which can pass through the filters are removed from the wash column 15 via the filters 27 and via a line 28. Larger crystals cannot however pass through the filters 27. A part of the mother liquor leaving the wash column 15 via the line 28 is recycled by means of a pilot pump 29, via a recycle line 30, into the upper region of the wash column 15. This makes it possible to regulate the hydraulic conditions in the wash column 15. The remaining liquid removed flows away via a line 31.

Figure 2:
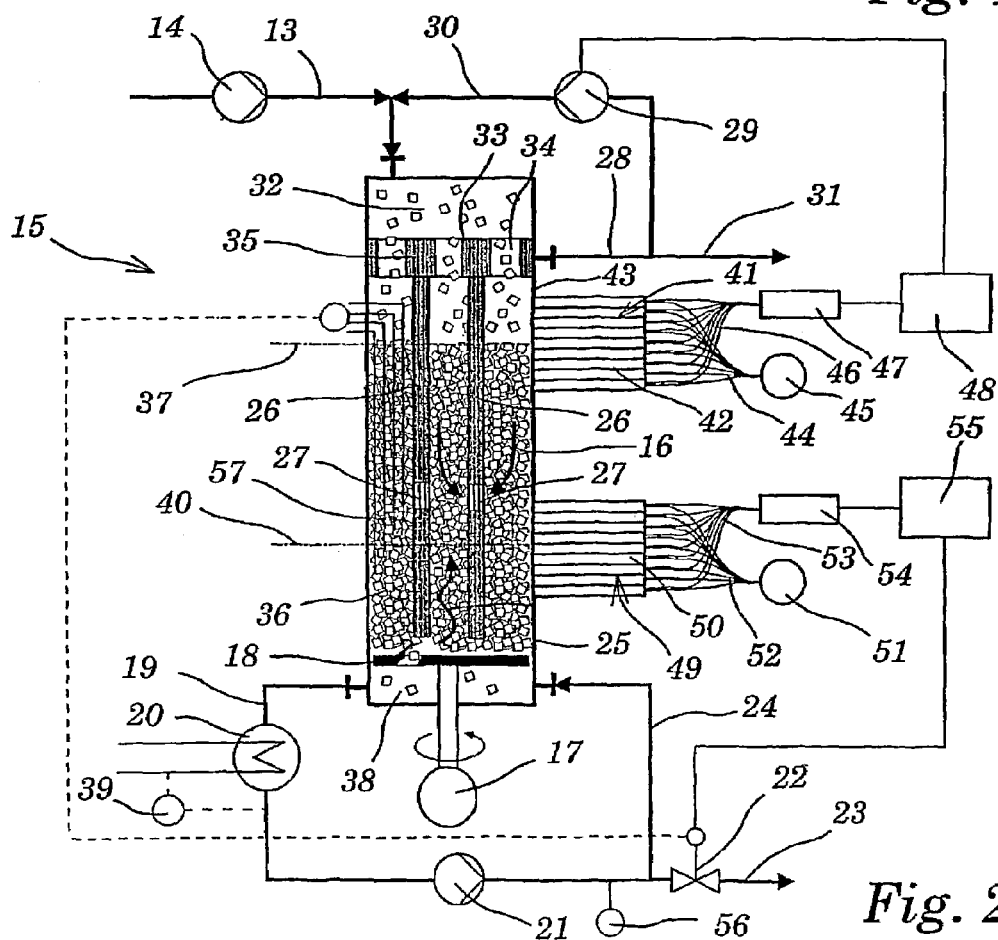
FIG. 2 shows a first embodiment of a novel apparatus.

FIG. 2 shows in more detail the design of a first embodiment of a novel wash column, as can be used in the plant of FIG. 1. Elements and components which have already been explained in connection with FIG. 1 are denoted by the same reference numerals and are not described in any more detail. In the example shown, as in the examples of FIGS. 3 and 4 below, the wash column 15 is in the form of a hydraulic wash column. The crystal suspension 32 removed from the crystallizer via the line 13 is fed by means of the pump 14 (or by means of hydrostatic pressure) into the wash column 15. Arranged in the upper part of the hydraulic wash column is a fluid register 33 which performs two functions: the suspension 32 is distributed over the cross-section of the wash column 15 via passages 34 from the upper to the lower part of the column. The continuous interior 35 of the fluid register serves as a collector for the liquids removed, in particular mother liquor and wash liquid. For this purpose, the abovementioned drainpipes 26, which communicate with the interior 35 of the fluid register 33, are arranged at the lower end of the fluid register 33. The drainpipes 26 have, at a defined height, the filters 27 through which the liquids are removed from the wash column.

After the wash column 15 has been started up, a compact crystal bed 16 forms. The crystal bed is transported past the filters 27 into a wash zone 36 below the filters by the force resulting from the hydraulic flow pressure drop of the mother liquor. The recycling of a part of the mother liquor back into the column by means of the pilot pump 29 permits regulation of this transport force. Variations in the crystal content of the suspension fed in or changes in the crystal size distribution which sustantially influence the flow pressure drop can thus be compensated. Such variations are detectable from changes in the position of the build-up front or filtration front, which is indicated in FIG. 2 by the dash-dot line 37. The filtration front 37 is distinguished by a relatively abrupt increase in the crystal content.

At the lower end of the wash column, the crystals are removed from the crystal bed 16 by means of the scraper 18 and are resuspended in the pure product melt. This suspension 38 is fed, in the melt circulation 19 described above in connection with FIG. 1, via the heat exchanger 20 which introduces the heat required for melting the crystals into the suspension. The corresponding heat introduction is usually likewise regulated as indicated schematically in FIG. 2 by the regulating device 39. A temperature regulator of the regulating device 39 ensures that the heat exchanger 20 only introduces so much energy into the circulation that the temperature directly downstream of the heat exchanger is 1 to 5 K. above the melting point of the pure product. Typically, 60-95% by weight of the melt are removed from the melt circulation 19 as purified pure product stream via the product valve 22. The remaining product melt flows through the crystal bed in the direction indicated by the arrow 25, with the result that countercurrent washing of the crystals is effected, and leaves the crystal bed via the filter 27.

In steady-state operation, a wash front, which is indicated by the dash-dot line 40 in FIG. 2, is established at a defined height of the wash zone 36. The wash front is defined as that location in the wash column where the highest temperature and concentration gradients occur. A concentration transition from mother liquor concentration (above the wash front) to pure melt concentration (below the wash front) occurs at the height of the wash front, in the liquid surrounding the crystal bed. The temperature of the fixed bed above the wash front corresponds roughly to the crystallization temperature of the starting liquid, while the temperature of the fixed bed below the wash front corresponds to the (higher) melting point of the pure substance. In the region of the wash front 40, there is therefore a temperature equilibration of the cold crystals with the pure wash liquid, during which the wash liquid partially or completely recrystallizes. That proportion of the wash liquid which has not recrystallized is lost via the filters 27. In order to achieve an adequate purification effect, the wash front 40 must be positioned at a specific minimum height above the scraper 18. The position of the wash front is therefore established as a dynamic equilibrium of the mother liquor transported with the fixed bed 16 and the countercurrent wash liquid stream (arrow 25).

According to the invention, line detectors are provided for regulating the position of the build-up or filtration front 37 and the position of the wash front 40. Thus, in the embodiment shown in FIG. 2, a first linear array 41 of reflection probes 42 is arranged in the side wall 43 of the wash column 15, in the region of the build-up front 37. Each of the reflection probes 42 has transmitting fibers 44, which are connected to a light source 45, and receiving fibers 46 which are connected to a detector 47. Light is directed into the crystal bed 16 via the transmitting fibers 44. The receiving fibers 46 pass the light reflected by the crystal bed to the detector 47, where the intensity of the reflected light is measured and recorded. The detector 47 can however also have a means (not shown) of a spectral analysis of the reflected light. A regulating device 48, which comprises, for example a computer, evaluates the signals delivered by the detector 47, determines the position of the build-up front and controls the pilot pump 29 so that the position of the build-up front 37 is kept at a specific setpoint position. If, in extreme operating states the regulating device finds that compensation of the disturbances via the pilot pump is no longer possible, a new setpoint position of the build-up front 37 which can be set under the given operating conditions may be determined, depending on the regulation strategy. This is permitted because a larger section of the column can be continuously monitored by the use, provided according to the invention, of a line detector. If, in the event of an operating fault, there is the danger that the build-up front will leave this monitored section and regulation will no longer be possible, it is also possible to trigger an alarm or to shut down the plant.

A corresponding second linear array 49 of reflection probes 50 is arranged in the cylindrical column wall 43, at the height of the wash front 40. Once again, light is directed into the crystal bed 16 via transmitting fibers 52 connected to a light source 51, and the light reflected from the crystal bed is passed to a detector 54 via receiving fibers 53. From the data delivered by the second reflection probe array 49, the position of the wash front 40 in the column 15 is determined by a control and regulation means 55 and the product valve 22 is set so that the wash front is kept at a specific setpoint position with high accuracy. If the regulating device detects a deviation in the wash front 40 from the setpoint height the pure product stream taken off and hence also the amount of wash liquid are correspondingly regulated via the product valve 22 (for example by increasing the amount of wash liquid if the wash front falls).

For maintaining and controlling the product purity, the quality of the pure product can however also be measured continuously. The measurement can be effected, for example, by means of an optical extinction sensor 56 which operates at a suitable spectral range, directly in the product line 23 or in a bypass. If the quality measurement (as illustrated in FIG. 2) is effected in the melt circulation 19, it can also be used for the startup of the wash column.

In addition to the regulation of the position of the wash front 40 by means of the line detector 49, regulation known per se by means of temperature sensors 57 can be realized. In particular cases where a purely optical determination of the position of the wash front is not reliably possible, it is then possible to rely on the data of the temperature sensors. It is of course also possible to determine only the position of the build-up front by means of the optical line detector 42 and to determine the position of the build-up front conventionally exclusively by means of the temperature sensors 57.

Figure 3:
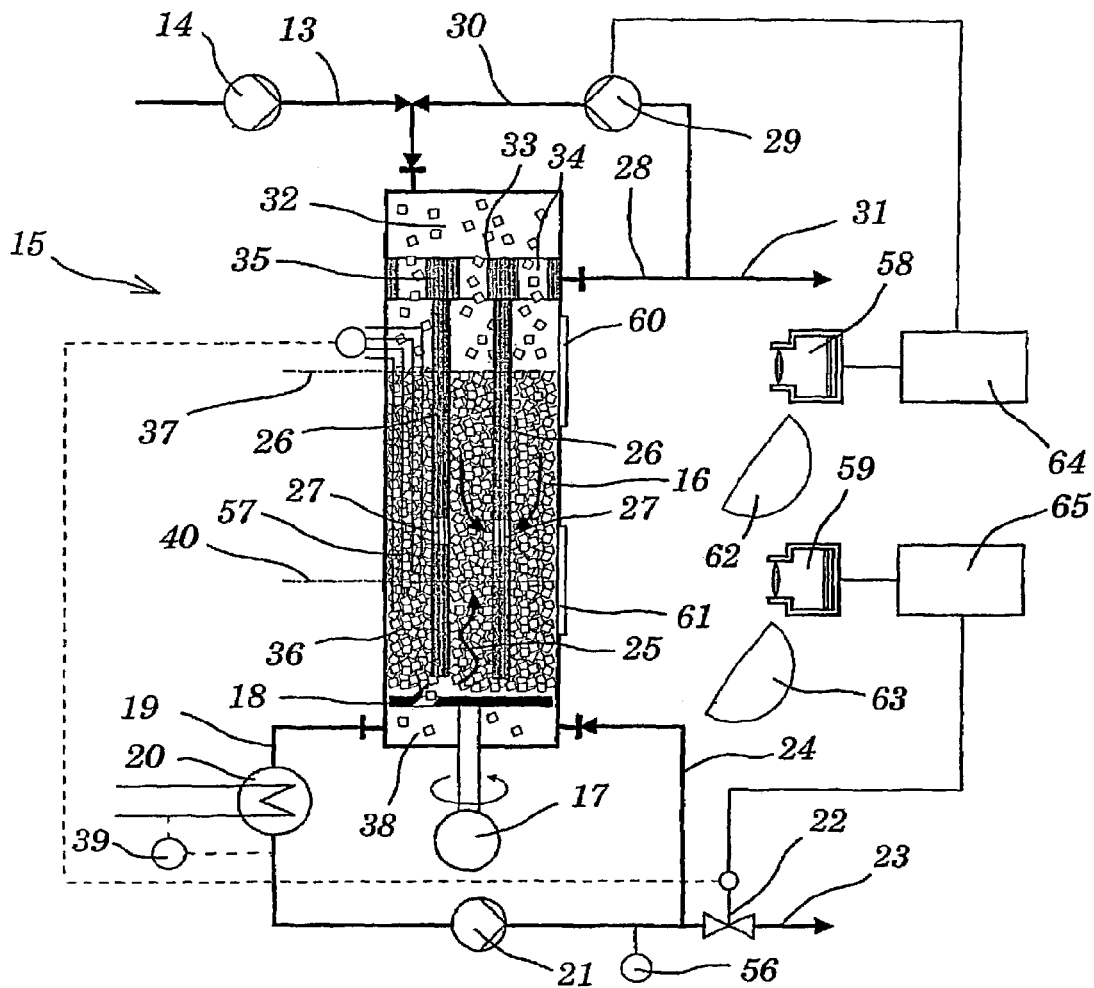
FIG. 3 shows a second embodiment of a novel apparatus.

FIG. 3 shows a second embodiment of the novel apparatus in which a line camera 58 for detecting the filtration front 37 and a line camera 59 for detecting the wash front 40 are each used as an optical line detector. The fundamental design of the wash column of FIG. 3 corresponds substantially to that of the wash column shown in FIG. 2. The corresponding components are provided with the same reference numerals and are explained below only briefly if at all. Elongated inspection windows 60, 61 which are focussed by the line cameras 58, 59 are arranged in the cylindrical side wall of the wash column 15, at the height of the wash front or of the filtration front. The windows 60, 61 can be illuminated by illumination means 62, 63. Evaluation means 64, 65 determine the position of the wash front 40 and the position of the build-up front 37 from the data of the line camera and control the pilot pump 29 or the product valve 22 so that the position of the fronts is kept at the respective setpoint positions.

Figure 4:
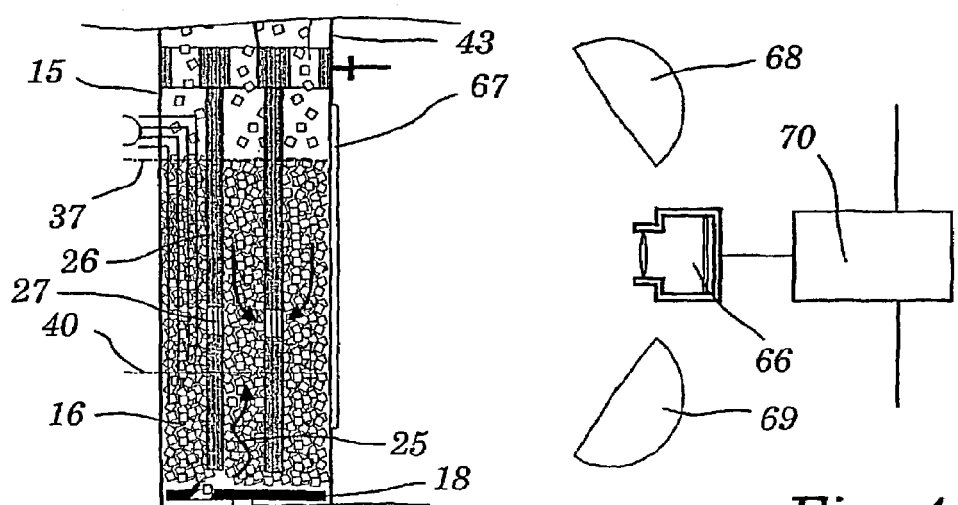
FIG. 4 shows a variant of the apparatus from FIG. 3.

FIG. 4 shows a variant of the embodiment of FIG. 3 in which only a single CCD line camera 66 is used for detecting wash and filtration front. For this purpose, the inspection window 67 provided in the wall 43 of the wash column 15 extends over the major part of the height of the wash column. If, for example, an axial section of a length of 2 m is captured by means of such an apparatus and the CCD camera uses as a sensor having 2048 linearly arranged pixels, regulation of the position of the wash front or of the position of the build-up front is also possible with an accuracy of from about 1 to 2 cm. The window 67 is illuminated by means of one or more light sources 68, 69. A control and regulation means 70 determines the position of the wash front or of the build-up front from the recorded data and sets the pilot pump or the product valve correspondingly.

When the term line detectors is used in the present description, this is associated with the fact that only a quasi one-dimensional measurement along the axis of the wash column is required for the novel regulation method. Of course, area detectors, for example conventional digital cameras having two-dimensional CCD chips, can also be used without disadvantages for realizing the novel method. The determination of the image region to be analyzed, for example of the region of the inspection window of the column 15, can be effected by commercial image processing software.

We claim:

1. A method for regulating a wash column in a melt crystallization process, comprising:
    regulating the position of a build-up front in the wash column by means of at least one optical line detector.

2. A method for regulating a wash column in a melt crystallization process in which
    a suspension, which contains, suspended in a mother liquor, crystals of a substance to be purified, is passed continuously into a wash column,
    a crystal bed of crystals of the substance to be purified forms in the wash column, the crystal bed having a build-up front at which crystals of the suspension passed and continuously accumulate,
    crystals are continuously removed at that end of the crystal bed which is opposite to the build-up front, the crystals removed are melted, a part of the melt is removed as pure product stream and another part of the melt is passed as a wash liquid stream through the crystal bed in the direction opposite to the transport direction of the crystals, a wash front forming in the crystal bed, wherein the position of the build-up front and/or of the wash front in the wash column is regulated by means of at least one optical line detector.

3. A method as claimed in claim 2, wherein the position of the wash front is measured by means of an optical line detector and is regulated to a setpoint position by controlling the pure product stream taken off.

4. A method as claimed in either of claims 2 and 3, a hydraulic wash column being used, wherein the position of the build-up front is measured by means of an optical line detector and is regulated to a setpoint position in the wash column by controlling the hydrodynamic pressure, which is neither a measured variable nor a control variable, or controlling the amount of liquid fed in above the build-up front.

5. A method as claimed in any of claims 2 and 3, wherein the line detector used comprises at least one linear array of fiber-optic reflection probes.

6. A method as claimed in any of claims 2 and 3, wherein the line detector used comprises at least one line camera, in particular a CCD line camera.

7. An apparatus for separating crystals and mother liquor in a suspension crystallization process, comprising
    a wash column which has at least one feed line for a crystal suspension, filtration means for removing mother liquor and means for removing crystals from a crystal bed at an end of the crystal bed which is opposite to a build up front at which crystals of the suspension passed in continuously accumulate,
    means for melting the crystals removed,
    a takeoff means for removing a part of the melt as pure product stream,
    at least one measuring means for determining the position of a build-up front and/or of a wash front of the crystal bed in the wash column,
    means for regulating the position of the build-up front and/or the position of the wash front,
    wherein the measuring means comprises at least one optical line detector.

8. An apparatus as claimed in claim 7, wherein the optical line detector comprises a linear array of fiber-optic reflection probes which are arranged in a wall of the wash column.

9. An apparatus as claimed in claim 7, wherein at least one transparent window is arranged in a wall of the wash column, and wherein the optical line detector comprises at least one line camera, in particular a CCD line camera.

10. An apparatus as claimed in claim 9, wherein the optical line detector comprises a color CCD line camera.

11. A method as claimed in claim 4, wherein the line detector used comprises at least one linear array of fiber-optic reflection probes.

12. A method as claimed in claim 4, wherein the line detector used comprises at least one line camera, in particular a CCD line camera.

13. An apparatus for separating crystals and mother liquor in a suspension crystallization process, comprising
    a wash column which has at least one feed line for a crystal suspension, a filtration mechanism for removing mother liquor and a removal mechanism for removing crystals from a crystal bed at an end of the crystal bed which is opposite to a build up front at which crystals of the suspension passed in continuously accumulate,
    a melting mechanism for melting the crystals removed,
    a takeoff mechanism for removing a part of the melt as pure product stream,
    at least one measuring mechanism for determining the position of a build-up front and/or of a wash front of the crystal bed in the wash column,
    a regulating mechanism for regulating the position of the build-up front and/or the position of the wash front,
    wherein the measuring mechanism comprises at least one optical line detector.

14. An apparatus as claimed in claim 13, wherein the optical line detector comprises a linear array of fiber-optic reflection probes which are arranged in a wall of the wash column.

15. An apparatus as claimed in claim 13, wherein at least one transparent window is arranged in a wall of the wash column, and wherein the optical line detector comprises at least one line camera, in particular a CCD line camera.

16. An apparatus as claimed in claim 15, wherein the optical line detector comprises a color CCD line camera.

17. A method for regulating a wash column according to claim 1, further comprising:
    regulating the position of a wash front in the wash column by means of at least one optical line detector.

18. A method for regulating a wash column in a melt crystallization process, comprising:
    regulating the position of a build-up front and/or of a wash-front in the wash column by emitting light onto said build-up front and/or said wash front and detecting light reflected by said build-up front and/or said wash front by at least one optical line detector.

* * * * *